United States Patent [19]

Gangjee

[11] Patent Number: 5,346,900

[45] Date of Patent: Sep. 13, 1994

[54] 5-ALKYL-6-[[AMINO]METHYL]PYRIDO[2,3-D]PYRIMIDINE DERIVATIVES AND METHODS OF USING THESE DERIVATIVES

[75] Inventor: Aleem Gangjee, Glenshaw, Pa.

[73] Assignee: Duquesne University of the Holy Ghost, Pittsburgh, Pa.

[21] Appl. No.: 950,982

[22] Filed: Sep. 23, 1992

Related U.S. Application Data

[63] Continuation of Ser. No. 829,519, Jan. 31, 1992, abandoned, which is a continuation of Ser. No. 682,043, Apr. 8, 1991, abandoned.

[51] Int. Cl.$^5$ .................. A61K 31/505; C07D 471/04
[52] U.S. Cl. ................................... 514/258; 544/279
[58] Field of Search ........................ 514/258; 544/279

[56] References Cited

U.S. PATENT DOCUMENTS 3,904,624  9/1975  Perronnet et al. ................. 544/279
4,831,037  5/1989  Taylor et al. ....................... 514/258

OTHER PUBLICATIONS

Rosowsky et al., J. Med Chem. vol. 34, 1991 pp. 1447–1454.
"Studies on Condensed Pyrimidine Systems. XXIII. Synthesis of 2,4-Diaminopyrido[2,3-d]pyrimidines from B-Keto Esters" *J. Med. Chem.*, vol. 11, pp. 703–707 (1968), B. S. Hurlbert et al.
"Studies on Condensed Pyrimidine Systems. XXIV. The Condensation of 2,4,6-Triaminopyrimidine with Malondialdehyde Derivatives" *J. Med. Chem.*, vol. 11, pp. 708–710 (1968), B. S. Hurlbert et al.
"Studies on Condensed Pyrimidine Systems. XXV. 2,4-Diaminopyrido [2,3-d]pyrimidines. Biological Data", *J. Med. Chem.*, vol. 11, pp. 711–717 (1968), B. S. Hurlbert et al.
"Synthesis and Antitumor Activity of 2,4-Diamino-6-(2,5-dimethoxybenzyl)-5-methylpyrido[2,3-d]pyrimidine", *J. Med. Chem.*, vol. 23, pp. 327–329 (1980), E. M. Grivsky et al.
"Folate Antagonists. 20. Synthesis and Antitumor and Antimalarial Properties of Trimetrexate and Related 6-[(Phenylamino)methyl]-2,4-quinazolinediamines", *J. Med. Chem.*, vol. 26, pp. 1753–1760 (1983), E. F. Elslager et al.
"Synthesis and Antifolate Activity of 5-Methyl-5-deaza Analogues of Aminopterin, Methotrexate, Folic Acid, and N$^{10}$-Methylfolic Acid", *J. Med. Chem.*, vol. 29, pp. 1080–1087 (1986), J. B. Piper et al.
"Synthesis and Antimalarial Activity of a Series of 2,4-Diamino-6-[(N-alkylanilino)methyl]quinazolines [1,2]", *J. Heterocyclic Chem.*, vol. 24, pp. 345–349 (1987), Leslie M. Werbel et al.

*Primary Examiner*—John M. Ford
*Assistant Examiner*—P. K. Sripada
*Attorney, Agent, or Firm*—Arnold B. Silverman; Jolene W. Appleman

[57] ABSTRACT

This invention discloses a compound and pharmaceutically acceptable salts having the formula:

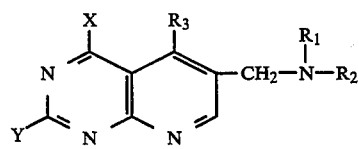

wherein X and Y are the same or different and are selected from the group consisting of OH and NH$_2$; wherein R$_1$ is selected from the group consisting of hydrogen, a first lower alkyl group, a nitroso group and an aldehyde; and wherein R$_2$ is selected from the group consisting of a second lower alkyl group which is the same as or different than the first lower alkyl group, an aryl group, an alkylaryl group, a substituted aryl group and a substituted alkylaryl group, and each substituent of the substituted aryl group or the substituted alkylaryl group is the same or different and is selected from the group consisting of a third lower alkyl group which is the same as or different than the first lower alkyl group or the second lower alkyl group, an alkoxy group, a substituted alkoxyaryloxy group and a halogen; and wherein R$_3$ is a fourth lower alkyl group which is the same as or different than said first lower alkyl group, said second lower alkyl group or said third lower alkyl group. Methods of preparing and using these compounds are disclosed.

15 Claims, 1 Drawing Sheet

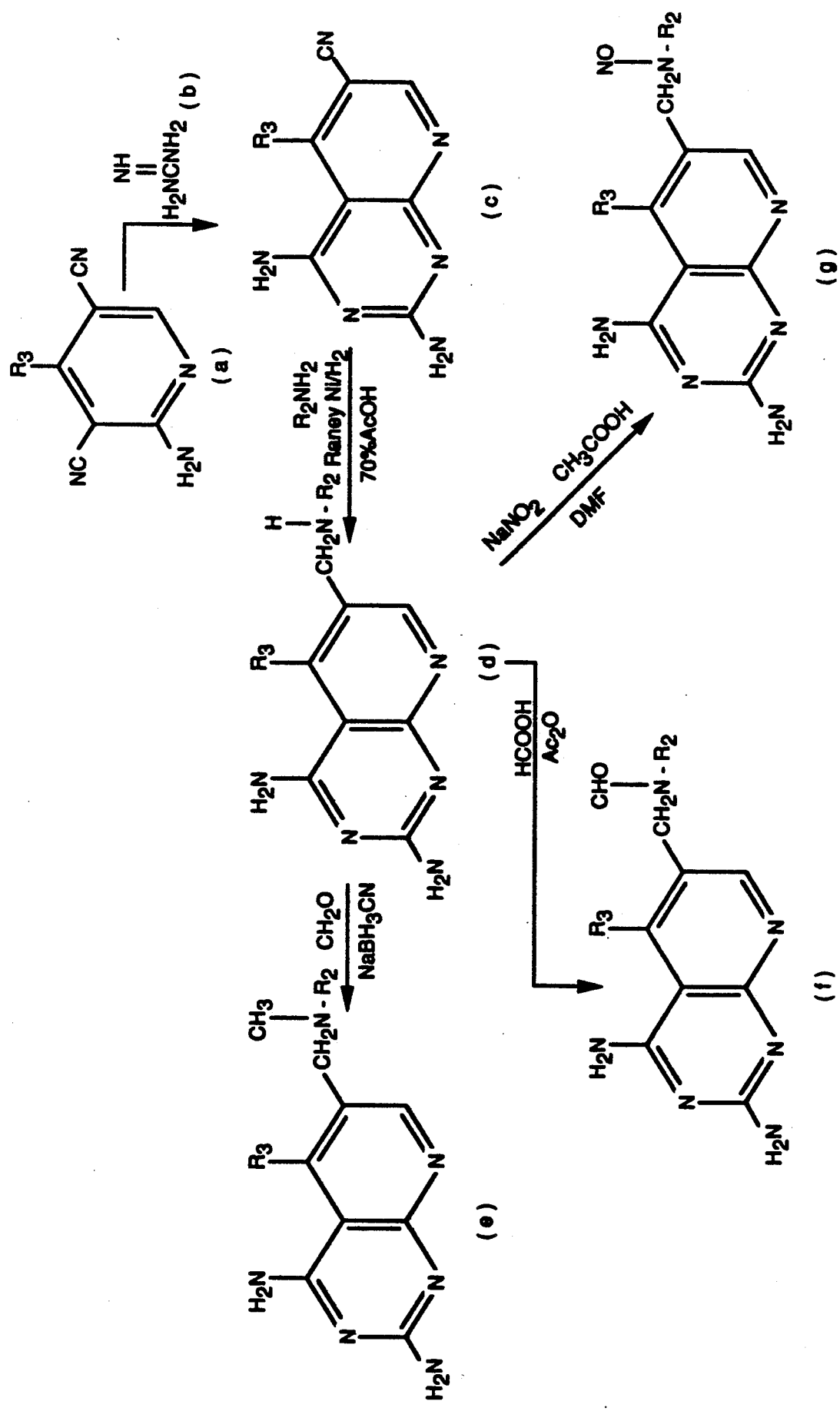

5-ALKYL-6-[[AMINO]METHYL]PYRIDO[2,3-D]-PYRIMIDINE DERIVATIVES AND METHODS OF USING THESE DERIVATIVES

The invention described herein was made in the course of work supported in part by the National Institutes of General Medical Sciences, Grant No. 1-R01-GM-40998 from the National Institutes of Health, U.S. Department of Health and Human Services. The Government has certain rights in this invention.

This application is a continuation of application Ser. No. 07/829,519, filed Jan. 31, 1992, now abandoned, which is a continuation of application Ser. No. 07/682,043, filed Apr. 8, 1991, now abandoned.

BACKGROUND OF THE INVENTION

1. Field of the Invention

This invention relates to 5-alkyl-6-[[amino]methyl]-pyrido[2,3-d]pyrimidine compounds and pharmaceutically acceptable salts thereof. More specifically, it relates to compounds useful in resisting *Pneumocystis carinii* and *Toxoplasmosis gondii* infections in immunocompromised patients, such as, for example, patients with autoimmune deficiency syndrome (AIDS). These compounds may be useful, for example, as potential antitumor, antibiotic, antimalarial, antifungal or antiprotozoal agents or as synergistic agents with sulfonamides and may require the use of leucovorin rescue. Methods of preparing and using these compounds are also provided.

2. Description of the Prior Art

The pyrido[2,3-d]pyrimidine ring system has been studied due to its involvement in the inhibition of dihydrofolate reductase (DHFR) enzymes activity. The pyrido [2,3-d]pyrimidine derivatives inhibit the normal cell growth of a variety of cells. Methotrexate (MTX), trimetrexate (TMX) and piritrexim and other folic acid analogues function as inhibitors of cell growth by similar mechanisms involving the inhibition of dihydrofolate reductase. Inhibition of dihydrofolate reductase deprives the cell of 5,10-methylenetetrahydrofolate. 5,10-methylenetetrahydrofolate is essential for cell growth. Dihydrofolate reductase reduces dihydrofolate to tetrahydrofolate. The inhibition of dihydrofolate reductase by the compounds and pharmaceutically acceptable salts of this invention results in the inhibition of DNA synthesis and leads to cell death.

Elslager, Edward F., et al., "Folate Antagonists. 20. Synthesis and Antitumor and Antimalarial Properties of Trimetrexate and Related 6-[(Phenylamino)methyl]-2,4-quinazolinediamines" *J. Med. Chem.*, Vol. 26 pp. 1753–1760 (1983), discloses the preparation of quinazolinediamines. This article states that the quinazolinediamines exhibit potent antimalarial, antibacterial and antitumor activity.

Methods to synthesize diaminopyrido[2,3-d]pyrimidines having various substituents are known. See Hurlbert, B. S., et al., "Studies on Condensed Pyrimidine Systems. XXIII. Synthesis of 2,4-Diaminopyrido[2,3-d]pyrimidines from β-Keto Esters", *J. Med. Chem.*, Vol. 11, pp. 703–707 (1968), and Hurlbert, B. S., and Valenti, B. F., "Studies on Condensed Pyrimidine Systems. XXIV. The Condensation of 2,4,6-Triaminopyridimine with Malondialdehyde Derivatives", *J. Med. Chem.*, Vol. 11, pp. 708–710 (1968).

Hurlbert, B. S., et al., "Studies on Condensed Pyrimidine Systems. XXV. 2,4-Diaminopyrido[2,3-d]pyrimidines. Biological Data", *J. Med. Chem.*, Vol. 11, pp. 711–717 (1968), discloses the antimicrobial activities of several subgroups of pyridopyrimidines. This article states that 2,4-diaminopyrido[2,3-d]pyrimidines bearing alkyl and aralkyl substituents in the pyrimidine moiety are inhibitors of dihydrofolate reductases having antibacterial and antiprotozoal activity and that these compounds potentiate sulfonamides.

Grivsky, E. M., et al., "Synthesis and Antitumor Activity of 2,4-Diamino-6-(2,5-dimethoxybenzyl)-5-methylpyrido[2,3-d]pyridimine", *J. Med. Chem.*, Vol. 23, pp. 327–329 (1980), discloses the synthesis of 2,4-diamino-6-(2,5-dimethoxybenzyl)-5-methylpyrido[2,3-d]pyridimine (BW301U,7). This article states that BW301U,7 is as effective as methotrexate as an inhibitor of dihydrofolate reductase purified from human leukemic cells and, in contrast to metoprine, has minimal activity as an inhibitor of histamine metabolism.

Werbel, Leslie M., et al., "Synthesis and Antimalarial Activity of a Series of 2,4-Diamino-6-[(N-alkylanilino)-methyl]quinazolines [1,2]", *J. Heterocyclic Chem.*, Vol. 24, pp. 345–349 (1987), discloses the synthesis of N6 substituted quinazoline dihydrofolate reductase inhibitors. This article states that these analogs demonstrate substantial activity against *Plasmodium berghei* infections in mice.

Piper, J. R., et al., "Syntheses and Antifolate Activity of 5-Methyl-5-deaza Analogues of Aminopterin, Methotrexate, Folic Acid, and N10-Methylfolic Acid". *J. Med. Chem.*, Vol. 29, pp. 1080–1087 (1986), discloses that 5-methyl-5-deaza analogues of aminopterin and methotrexate are much more growth inhibitory than methotrexate.

In spite of the prior art disclosures, there remains a very real and substantial need for an inhibitor of dihydrofolate reductases that is more active and more selective than known compounds having antitumor, antibiotic, antimalarial, antifungal or antiprotozoal activity or as synergistic agents with sulfonamides, and for methods of preparing and using such compounds.

SUMMARY OF THE INVENTION

The present invention has met the hereinbefore described need. The present invention provides compounds and pharmaceutically acceptable salts having a formula (1):

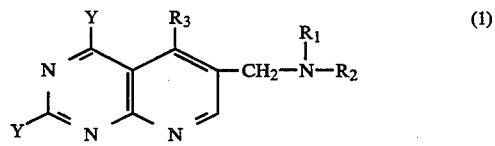

wherein X and Y may be the same or different and are selected from the group consisting of OH and $NH_2$; wherein $R_1$ is selected from the group consisting of hydrogen, a first lower alkyl group, a nitroso group and an aldehyde; and wherein $R_2$ is selected from the group consisting of a second lower alkyl group which is the same as or different than the first lower alkyl group, an aryl group, an alkylaryl group, a substituted aryl group and a substituted alkylaryl group, and each substituent of the substituted aryl group or the substituted alkylaryl group is the same or different and is selected from the group consisting of a third lower alkyl group which is the same as or different than the first lower alkyl group or the second lower alkyl group, an alkoxy group, a substituted alkoxyaryloxy group, and a halogen; and wherein $R_3$ is a fourth lower alkyl group which is the same as or different than the first lower alkyl group, the second lower alkyl group or the third lower alkyl group.

Pharmaceutically acceptable salts include, for example, acetate, formate, glucuronate, ethantate or ethansulfonate.

In formula 1, when X and Y are the same or different and are selected from the group consisting of OH and $NH_2$ groups, the enol form of the compounds is represented. The enol form is equivalent to and includes the keto form of the compounds.

This invention also provides a method for preparing the compounds and pharmaceutically acceptable salts described herein.

This invention provides a process of using the 5-alkyl-6-[[amino]methyl]pyrido[2,3-d]pyrimidine derivatives described herein for therapeutic purposes including employing these compounds as antitumor, antibiotic, antimalarial, antifungal and antiprotozoal agents and as synergistic agents with sulfonamides. The 5-alkyl-6-[[amino]methyl]pyrido[2,3-d]pyrimidine compounds and pharmaceutically acceptable salts of this invention substantially inhibit dihydrofolate reductase enzymes. This invention provides a process of using 5-alkyl-6[[amino]methyl]pyrido[2,3-d]pyrimidine derivatives for therapeutic purposes as an antiprotozoal agent effective against secondary infections caused by *Pneumocystis carinii* and *Toxoplasmosis gondii* in immunocompromised patients such as for example patients with AIDS.

This invention provides a process for using the compounds and pharmaceutically acceptable salts described herein for prophylactic purposes including employing these compounds as antitumor, antibiotic, antimalarial, antifungal and antiprotozoal agents and as synergistic agents with sulfonamides. This invention provides a process of using these compounds for prophylactic purposes as an antiprotozoal agent effective against secondary infections caused by *Pneumocystis carinii* and *Toxoplasmosis gondii* in immunocompromised patients such as for example patients with AIDS.

It is an object of this invention to provide 5-alkyl-6-[[amino]methyl]pyrido[2,3-d]pyrimidine compounds and pharmaceutically acceptable salts for substantially inhibiting dihydrofolate reductase enzymes.

It is an object of the present invention to provide 5-alkyl-6-[[amino]methyl]pyrido[2,3-d]pyrimidine compounds and pharmaceutically acceptable salts having antitumor, antibiotic, antimalarial, antifungal or antiprotozoal activity or synergistic activity with sulfonamides.

It is a further object of this invention to provide 5-alkyl-6-[[amino]methyl]pyrido[2,3-d]pyrimidine compounds and pharmaceutically acceptable salts having effective activity against secondary infections, such as for example infections caused by *Pneumocystis carinii* and *Toxoplasmosis gondii* that occur in immunocompromised patients, such as for example patients with AIDS.

It is an object of this invention to provide a method of preparing 5-alkyl-6-[[amino]methyl]pyrido[2,3-d]pyrimidine compounds and pharmaceutically acceptable salts thereof.

It is a further object of this invention to provide a method of using in a patient a therapeutically effective amount of 5-alkyl-6-[[amino]methyl]pyrido[2,3-d] pyrimidine compounds and pharmaceutically acceptable salts thereof.

It is a further object of this invention to provide a method of using in a patient a prophylactically effective amount of 5-alkyl-6-[[amino]methyl]pyrido[2,3-d]pyrimidine compounds and pharmaceutically acceptable salts thereof.

These and other objects of the invention will be more fully understood from the drawing and the following description of the invention and the claims appended hereto.

BRIEF DESCRIPTION OF THE DRAWING

FIG. 1 shows a schematic diagram of the general chemical structure of the compounds and derivatives of this invention and the method of preparing these compounds and derivatives.

DESCRIPTION OF THE PREFERRED EMBODIMENT

As used herein, the term "patients" means members of the animal kingdom including but not limited to human beings.

The 5-alkyl-6-[[amino]methyl]pyrido[2,3-d]pyrimidine derivatives and pharmaceutically acceptable salts and methods of preparing and using the compounds of this invention provide antitumor, antibiotic, antifungal antimalarial and antiprotozoal agents, and synergistic agents with sulfonamides. The compounds of this invention provide for the therapeutic and prophylactic treatment of secondary infections caused by *Pneumocystis carinii* and *Toxoplasmosis gondii* in immunocompromised patients, such as for example patients having a primary infection caused by a retrovirus including human immunodeficiency virus (HIV).

The 5-alkyl-6-[[amino]methyl]pyrido[2,3-d]pyrimidine compounds and pharmaceutically acceptable salts of this invention inhibit the dihydrofolate reductase (DHFR) enzymes. The DHFR enzymes are needed for normal cell growth. It is known by those skilled in the art that 5,10-methylenetetrahydrofolate is essential for cell growth. It is also well known to those skilled in the art that dihydrofolate reductase reduces dihydrofolate to tetrahydrofolate. The derivatives of the present invention inhibit dihydrofolate reductase and consequently inhibit DNA synthesis. Inhibition of DNA synthesis results in cell death. The compounds and pharmaceutically acceptable salts of this invention have the formula (1):

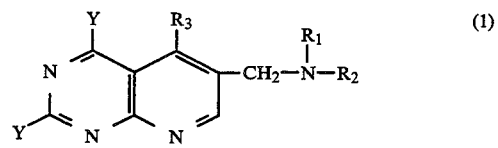

wherein X and Y are the same or different and are selected from the group consisting of OH and $NH_2$. $R_1$ is selected from the group consisting of hydrogen, a first lower alkyl group, a nitroso group and an aldehyde. $R_2$ is selected from the group consisting of a second lower alkyl group which is the same as or different than the first lower alkyl group, an aryl group, an alkylaryl group, a substituted aryl group and a substituted alkylaryl group. Each substituent of the substituted aryl group or the substituted alkylaryl group is the same or different and is selected from the group consisting of a third lower alkyl group which is the same as or different than the first lower alkyl group or the second lower alkyl group, an alkoxy group, a substituted alkoxyaryloxy group and a halogen; and wherein $R_3$ is a fourth lower alkyl group which is the same as or different than the first lower alkyl group, the second lower alkyl group or the third lower alkyl group.

The first, second, third and fourth lower alkyl groups are the same or different and are groups having one to about seven carbon atoms, such as for example methyl, ethyl, propyl, butyl, pentyl, hexyl or heptyl groups. These lower alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

Suitable aryl groups include for example phenyl and benzyl groups. Suitable substituted aryl groups include for example: mono-, di- and tri-substituted alkoxy phenyl groups; mono-, di and tri-halogenated phenyl groups; mono-, di- and tri-substituted alkyl phenyl groups; mono-, di- and tri-substituted alkoxy benzyl groups; and mono-, di-, and tri-substituted halogenated benzyl groups.

The term "alkylaryl" refers to groups having an alkyl moiety attached to an aryl ring such as a phenyl or benzyl ring. The alkyl moiety is preferably a lower alkyl chain having one to about seven carbon atoms. This alkyl moiety may also contain oxygen, nitrogen or sulfur atoms, such as for example methoxy groups. The aryl moiety of the alkylaryl group is unsubstituted, monosubstituted, disubstituted or trisubstituted. If substituted, each substituent may independently be selected from the group consisting of a lower alkyl group having one to about seven carbon atoms, an alkoxy group such as for example a methoxy group and a halogen, such as for example fluorine, chlorine or bromine.

Pharmaceutically acceptable salts include for example acetate, formate, glucuronate, ethantate or ethansulfonate.

In the general formula 1 wherein X and Y are the same or different and are selected from the group consisting of OH and $NH_2$ groups, the enol form of the compounds of this invention is represented. This enol form is equivalent to and includes the keto form of the compounds of this invention.

In a most preferred embodiment of this invention, compounds and pharmaceutically acceptable salts are provided having the formula 1 and (a) wherein X and Y are each $NH_2$, $R_1$ is H, $R_2$ is 3,4,5-trimethoxyphenyl and $R_3$ is $CH_3$ (Compound I), or (b) wherein X and Y are each $NH_2$, $R_1$ is $CH_3$, $R_2$ is 3,4,5-trimethoxyphenyl and $R_3$ is $CH_3$ (Compound II), or (c) wherein X and Y are each $NH_2$, $R_1$ is CHO, $R_2$ is 3,4,5-trimethoxyphenyl and $R_3$ is $CH_3$ (Compound III). Compounds I, II and III and pharmaceutically acceptable salts are preferred in resisting secondary infections caused by *Pneumocystis carinii* and *Toxoplasmosis gondii* in immunocompromised patients.

In a preferred embodiment of this invention, compounds and pharmaceutically acceptable salts are provided having the formula 1 wherein X and Y are each $NH_2$. $R_1$ is selected from the group consisting of H, $CH_3$ and CHO, and $R_2$ is selected from the group consisting of 2,5-dimethoxyphenyl, 2,3,4-trimethoxyphenyl, 2,4,6-trimethoxyphenyl, 2,3-dichlorophenyl, 2,4-dichlorophenyl, 2,5-dichlorophenyl, 2,6-dichlorophenyl, 3,4-dichlorophenyl and 3,5-dichlorophenyl. $R_3$ is $CH_3$.

In another embodiment of this invention, compounds and pharmaceutically acceptable salts are provided having the formula 1 wherein X and Y are each $NH_2$. $R_1$ is selected from the group consisting of H, $CH_3$, NO and CHO. $R_2$ is selected from the group consisting of 2-methoxyphenyl, 3-methoxyphenyl, 4-methoxyphenyl, 2,4-dimethoxyphenyl, 3,4-dimethoxyphenyl, 3-5-dimethoxyphenyl, 2-chlorophenyl, 3-chlorophenyl, 4-chlorophenyl, 2,3,4-trichlorophenyl, 2,4,5-trichlorophenyl, 2,4,6-trichlorophenyl, 3,4,5-trichlorophenyl, 2-bromophenyl, 3-bromophenyl, 4-bromophenyl, 2,4-dibromophenyl, 2,5-dibromophenyl, 2,6-dibromophenyl, 3,4-dibromophenyl, 3,5-dibromophenyl, 2,4,6-tribromophenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,4,5-trifluorophenyl, 2,4,6-trifluorophenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, and 2,4,6-trimethylphenyl. $R_3$ is $CH_3$.

In a less preferred embodiment of this invention, compounds and pharmaceutically acceptable salts are provided having the formula 1 wherein X and Y are each $NH_2$. $R_1$ is selected from the group consisting of H, $CH_3$, NO and CHO. $R_2$ is selected from the group consisting of methyl, ethyl, n-propyl, n-butyl, cyclopropyl, cyclobutyl, cyclopentyl, cyclohexyl, 2-methoxybenzyl, 3,4-dimethoxybenzyl, 2,3-dimethoxybenzyl, 3,4-dimethoxybenzyl, 2,3,4-trimethoxybenzyl, 3,4,5-trimethoxybenzyl, 2-chlorobenzyl, 3,4-dichlorobenzyl, 2,3-dichlorobenzyl, 2,4-dichlorobenzyl, 2,5-dichlorobenzyl, 2,6-dichlorobenzyl, 2,6-dichlorobenzyl, 3,4-dichlorobenzyl, 3,5-dichlorobenzyl, 2-bromobenzyl, 3,4-dibromobenzyl, 2-fluorobenzyl, 3,4-difluorobenzyl, 2,4-difluorobenzyl, 2,5-difluorobenzyl, 2,6-difluorobenzyl and 3,4-difluorobenzyl. $R_3$ is $CH_3$.

EXAMPLE I

Compounds I, II and III were evaluated as inhibitors of dihydrofolate reductases (DHFR) from *Pneumocystis carinii* (Pc) and *Toxoplasmosis gondii* (Tx) and rat liver (RL). Compounds I, II and III were compared in this respect with trimetrexate. Trimetrexate is available from Warner-Lambert/Parke Davis Pharmaceutical Research, Ann Arbor, Mich. Trimetrexate is approved by the United States Food and Drug Administration as an investigational new drug for the treatment of *Pneumocystis carinii* infections in patients with AIDS.

The evaluations of Compounds I, II and III consisted of determining the $IC_{50}$ values and selectivity ratios of each compound. The $IC_{50}$ value is the concentration of a compound required to inhibit the dihydrofolate reductase activity by 50 percent (%). It will be understood by those skilled in the art that the lower the $IC_{50}$ value the more potent the compound. The selectivity ratio is a measure of the selectivity of a compound for Pc DHFR or Tx DHFR and is expressed as the $IC_{50}$ value of the DHFR from rat liver (RL) divided by the $IC_{50}$ value of the DHFR of *Pneumocystis carinii* (Pc) or *Toxoplasmosis gondii* (Tx). For example, the selectivity ratio of a compound is calculated by the following formula (2):

$$\frac{IC_{50} \; RL \; DHFR}{IC_{50} \; (Pc \; DHFR \; or \; Tx \; DHFR)} \qquad (2)$$

It will be understood by those skilled in the art that the higher the number of the selectivity ratio, the less toxic the compound is to mammalian dihydrofolate reductases, and thus, less toxic.

Table I sets forth the $IC_{50}$ values for Pc DHFR, RL DHFR and Tx DHFR and the corresponding selectivity ratios for Compounds I, II, III and trimetrexate.

TABLE I

|  | Pc DHFR[1] | RL DHFR[1] | Selectivity Ratio: RL DHFR/Pc DHFR | Tx DHFR[1] | Selectivity Ratio: RL DHFR/Tx DHFR |
|---|---|---|---|---|---|
| Compound I | 86.0 | 2.1 | 0.02 | 7.4 | 0.28 |
| Compound II | 13.2 | 7.6 | 0.58 | 0.85 | 8.94 |
| Compound III | 550.0 | 110.0 | 0.20 | 13.0 | 8.46 |
| Trimetrexate | 42.0 | 3.0 | 0.072 | 10.0 | 0.29 |

[1] Values are $IC_{50}$ in nanomoles (nM). One nanomole = $1 \times 10^{-9}$ mole.

From Table I, it will be appreciated that Compounds I, II, and III are each potent inhibitors of all the DHFRs tested.

Table I shows that Compound I has an $IC_{50}$ value of 86 nM (nanomoles) and is generally about two times less active than trimetrexate on *Pneumocystis carinii* DHFR and has about the same activity as trimetrexate on *Toxoplasmosis gondii* DHFR. The selectivity ratio of 0.02 of Compound I for Pc DHFR is less than trimetrexate but the selectivity ratio of 0.28 of Compound I for Tx DHFR is generally equal to trimetrexate.

Compound II is the most active and the most selective of the four compounds tested. Compound II with an $IC_{50}$ value of 13.2 nM is more than three times more active than trimetrexate on Pc DHFR and has a selectivity ratio of 0.58 which is about eight times less toxic than trimetrexate. In Tx DHFR, Compound II with an $IC_{50}$ value of 0.85 nM is about twelve times more active than trimetrexate and has a selectivity ratio of 8.94 which is about thirty-one times less toxic than trimetrexate. Compound II is the most potent analogue known at the present time with regard to Tx DHFR inhibition.

Compound III with an $IC_{50}$ value of 550 nM is about thirteen times less active than trimetrexate in Pc DHFR and has a selectivity ratio of 0.20 which is about three times less toxic than trimetrexate. However, Compound III with an $IC_{50}$ value of 13 nM has about the same activity as trimetrexate in Tx DHFR but has a selectivity ratio of 8.46 which is about twenty-nine times less toxic than trimetrexate.

These results indicate that the compounds of this invention are significantly active in Pc DHFR and in Tx DHFR and that Compound II is the most preferred compound of this invention for the treatment of infections caused by *Pneumocystis carinii* and *Toxoplasmosis gondii*. With regard to *Toxoplasmosis gondii*, Compound II with its high potency and high selectivity may be used clinically with a lesser amount of leucovorin or may be used clinically without the necessity of leucovorin, and thus greatly reduce the cost of administering this compound to a patient.

A further embodiment of this invention provides methods for preparing the hereinbefore described compounds and pharmaceutically acceptable salts thereof. The method of preparing the compounds and pharmaceutically acceptable salts of this invention is set forth generally in FIG. 1 and includes condensing 2-amino-3,5-dicarbonitrile-4-$R_3$-pyridine (represented by the letter "a" in FIG. 1) wherein $R_3$ is a lower alkyl group having one to about seven carbon atoms as described herein, such as for example, a methyl group, with guanidine (FIG. 1b) in refluxing ethyl alcohol to produce 2,4-diaminopyrido[2,3-d]pyrimidine-5-$R_3$-6-carbonitrile (FIG. 1c), subjecting 2,4-diaminopyrido[2,3-d]pyrimidine-5-$R_3$-6-carbonitrile (FIG. 1c) to reductive condensation with an alkyl amine, a substituted aniline or benzylamine derivative containing the $R_2$ group as described herein, such as for example, 3,4,5-trimethoxyaniline, and Raney nickel in aqueous acetic acid solution, and preferably about 70% acetic acid solution, to form 2,4-diamino-5-$R_3$-6-[[($R_2$)amino]methyl]-pyrido[2,3-d]pyrimidine (FIG. 1d). The starting material 2-amino-3,5-dicarbonitrile-4-$R_3$-pyrimidine (FIG. 1a) may be synthesized by those skilled in the art by modifying the method of Piper, et al., *J. Med. Chem.*, Vol. 29, p. 1080 (1986).

These methods further include adding product "d" to about 37% formaldehyde in acetonitrile at about 25° Centigrade (C.), adding sodium cyanoborohydride, glacial acetic acid and methanol, and refrigerating the reaction mixture overnight to form 2,4-diamino-5-$R_3$-6[[($R_2$)methylamino]methyl]pyrido[2,3-d]pyrimidine (FIG. 1e).

A method to prepare 2,4-diamino-5-$R_3$-6[[($R_2$)formylamino]methyl]pyrido[2,3-d]pyrimidine (FIG. 1f) includes reacting product "d" in about 98% formic acid as a solvent and acetic anhydride as a catalyst, removing the solvent under reduced pressure, diluting the reaction product with methanol and refrigerating the diluted reaction product overnight.

A method to prepare 2,4-diamino-5-$R_3$-6[[($R_2$)nitrosoamino]methyl]pyrido[2,3-d]pyrimidine (FIG. 1g) includes reacting a chilled solution of product "d" in aqueous acetic acid and dimethyl formamide (DMF) and then adding $NaNO_2$ (sodium nitrate) in water. This mixture is stirred at about 0° C. to 5° C. for about two hours and then poured into dilute-sodium hydroxide.

It will be appreciated by those skilled in the art that by following the hereinbefore described methods of preparing products d, e, f and g of this invention that the derivatives of products d, e, f and g can be similarly prepared using the appropriate alkylamine, substituted aniline or benzylamine derivative containing the $R_2$ group as described herein.

Further, a method for preparing 4-amino-4-oxo derivatives of products d, e, f or g of this invention includes subjecting products d, e, f or g, respectively, to hydrolysis with 6N (six-normal solution) HCl for about six hours at room temperature.

Another embodiment of this invention is a method for preparing 2,4-dioxo derivatives of products d, e, f or g that includes subjecting product d, e, f or g, respectively, to hydrolysis with 6N HCl under mild reflux conditions for about two hours.

In order to further disclose a preferred method of preparing products d, e, f or g and derivatives thereof, the following examples are provided. Examples II, III and IV disclose methods of preparing Compounds I, II and III, respectively.

EXAMPLE II

Compound I was made in the following manner. Dried and pulverized guanidine hydrochloride (30.9 g; 0.323 mol.) was added to a solution prepared by dissolving Na metal (7.44 g; 0,323 mol.) in absolute ethyl alcohol (1.5 liter). This mixture was stirred rapidly at about 25° C. for about 30 minutes, and then 2-amino-3,5-dicarbonitrile-4-methylpyridine (24.7 g; 0.56 mol.) was added. The resulting mixture was refluxed with stirring for about seven days. The ethyl alcohol insoluble product (2,4-diamino-5-methylpyrido[2,3-d]pyrimidine-6-carbonitrile) and NaCl were filtered from the boiling mixture. The solid cake was then stirred with boiling ethyl alcohol, washed with hot water, ethyl alcohol and Et$_2$O (ethyl ether) in that order to yield pure 2,4-diamino-5-methylpyrido[2,3-d]pyrimidine-6-carbonitrile in 65% yield and having a melting point greater than 300° C. A stirred solution of 2,4-diamino-5-methylpyrido[2,3-d]pyrimidine-6-carbonitrile (3.5 g; 17.5 mmol) and trimethoxyaniline (4.6; 2.51 mmol) in about 70% acetic acid (600 ml) containing damp Raney Ni (about 10 g) was kept under H$_2$ at atmospheric pressure for about 24 hours. The mixture was then treated with Norit and filtered (celite mat). Acetic acid was removed from the filtrate by evaporation under reduced pressure (H$_2$O aspirator, bath at 40° C.) with the aid of added portion of ethanol. Then a solution of the residue, in warm ethanol (20 ml), was added in a thin stream to a stirred saturated sodium carbonate solution (200 ml) at room temperature. The mixture was stirred at about 10° C. for about 20 minutes and the yellow precipitate that formed was collected, washed with H$_2$O and dried. The crude product contained unchanged trimethoxyaniline, which was removed by repeated treatment with acetone and methanol (50 ml). The insoluble material was suspended and stirred in about 200 ml of ethanol for about 1 hour. The solid was collected by filtration, and dissolved in glacial acetic acid. The cloudy solution was clarified (using celite), concentrated, diluted with methanol (80 ml) and left for about 16 hours in a refrigerator when the desired product 2,4-diamino-5-methyl-6[[(3,4,5-trimethoxyphenyl)amino]methyl]pyrido[2,3-d]pyrimidine (Compound I) separated as a yellow solid (2.2 g) at a yield of 38.5%. 1HNMR $\delta$ 2.65(s, 3H, CH$_3$), 3.56 (s,3H, OCH$_3$), 3.67 (s, 6H, 2OCH$_3$), 4.17 (S,CH$_2$, 2H), 5.66 (t, 1H, exchangeable), 5.93 (s, 2H, Ar-H), 6.21 (s, 2H, exchangeable), 6.99 (s,2H,exchangeable), 8.48 (s, 1H, aromatic H's). Microanalyses calculated for C$_{18}$H$_{22}$N$_6$O$_3$.0.4 CH$_3$COOH.2H$_2$O. C 52.46, H 6.46, N 19.52; Found C 52.60, H 6.22, N 19.71

EXAMPLE III

Compound II was made in the following manner. To a stirred suspension of Compound I (0.5 g; 1.35 mmol) and about 37% formaldehyde (0.5 ml) in acetonitrile (10 ml) at about 26° C. was added sodium cyanoborohydride (0.25 g, 4.05 mmol). Glacial acetic acid (0.1 ml) was added to the reaction mixture. After stirring about 2 hours, additional glacial acetic acid (0.2 ml) was added, and the mixture was stirred for about 48 hours. The reaction mixture was diluted with methanol, and refrigerated overnight. The solid 2,4-diamino-5-methyl-6-[[(3,4,5-trimethoxyphenyl)methylamino] pyrido[2,3-d]pyrimidine (Compound II) (0.22 g) was collected by filtration, and the residue was washed with H$_2$O, methanol and ether to afford a yield of 42% of Compound II which had a melting point greater than 300° C. 1HNMR $\delta$ 1.85 (s, 3H, CH$_3$), 2.6 (s, 3H, N-CH$_3$), 3.5 (s, 3H, OCH$_3$), 3.7 (S,6H, 2OCH$_3$), 4.47 (s, 2H, CH$_2$), 6.05 (s, 2H, At-H), 6.20 (s, 2H, NH$_2$, exchangeable), 6.98 (s, 2H, NH$_2$, exchangeable), 8.2(s, 1H, aromatic's H). Microanalyses calculated for C$_{19}$H$_{24}$N$_6$O$_3$.0.3 H$_2$O. C 59.36, H 6.29, N 21.86; Found C 59.54, H 6.36, N 21.56.

EXAMPLE IV

Compound III was made in the following manner. A suspension of Compound I (0.3 g; 0.81 mmol) in about 98% formic acid as a solvent (3 ml) was stirred at about 25° C. for about 5 hours and the solvent was removed under reduced pressure. The residue was diluted with methanol and refrigerated overnight. The off-white solid 2,4-diamino-5-methyl-6-[[(3,4,5-trimethoxyphenyl)formylamino]methyl]pyrido[2,3-d]pyrimidine (Compound III) (0.3 g) was collected as a formic acid salt (formate) at a yield of 75%, and had a melting point greater than 300° C. 1HNMR $\delta$ 2.65 (s, 3H, CH$_3$), 3.65 (s, 3H, OCH$_3$), 3.74 (s, 6H, 2OCH$_3$), 5.1 (s, 2H, CH$_2$), 6.65 (s, 2H, At-H), 6.6 (s, 2H, NH$_2$, exchangeable) 7.3 (s, 2H exchangeable), 8.15 (s, 1H, aromatic H's), 8.4 (s, 1H, CHO), 8.5 (s,1H, CHO). Microanalyses calculated for C$_{19}$H$_{23}$N$_6$O$_4$.1.0 HCOOH. C 53.93, H 5.66, N 18.87; Found C 53.59, H 5.48, N 18.96.

Another embodiment of this invention provides a method of using the compounds and pharmaceutically acceptable salts of this invention for therapeutic purposes. This process includes incorporating a compound of this invention in a suitable pharmaceutical carrier and administering a therapeutically effective amount of the compound of this invention to a patient.

Another embodiment of this invention provides a method of using the compounds and pharmaceutically acceptable salts of this invention for prophylactic purposes. This process includes incorporating a compound of this invention in a suitable pharmaceutical carrier and administering a prophylactically effective amount of the compound of this invention to a patient.

Examples of suitable pharmaceutical carriers are physiologic saline (0.9% Sodium Chloride) and 5% dextrose injection. The compounds of this invention incorporated into the pharmaceutical carrier may be administered to a patient by parenteral injection, such as for example intravenously, intrathecally, intramuscularly or intraarterially. Other potential routes of administration include, for example, orally or topically. The dosage of, route of administration of and duration of therapy with the compounds and pharmaceutically acceptable salts of this invention will be individualized according to the disease state and/or infection being treated, body weight of the patient, other therapy employed in conjunction with the compounds of this invention and the condition, clinical response and tolerance of the patient.

It will be understood by those skilled in the art that the compounds and pharmaceutically acceptable salts described herein may be used as synergistic agents with other compounds.

It will be appreciated by those skilled in the art that the compounds and the pharmaceutically acceptable salts of this invention may be used to transport other compounds, such as for example azidothymidine which is also known as AZT, across the blood-brain barrier for distribution in the cerebrospinal fluid. AZT is commercially known as Zidovudine (Retrovir ®) and is available from Burroughs Wellcome, 3030 Cornwallis Road, Research Triangle Park, N.C. 27709. It will be appreciated by those skilled in the art that both the transported compound and the compound of this invention will be active in the cerebrospinal fluid after crossing the blood brain barrier.

It will be appreciated by those skilled in the art that this invention provides compounds and pharmaceutically acceptable salts thereof effective against infections caused by *Pneumocystis carinii* and *Toxoplasmosis gondii*, a method of preparing these compounds, and a method of using these compounds in a patient for therapeutic or prophylactic purposes.

Whereas, particular embodiments of this invention have been described above for purposes of illustration, it will be evident to those skilled in the art that numerous variations of the details of the present invention may be made without departing from the invention as defined in the appended claims.

We claim:

1. A compound and pharmaceutically acceptable salts having the formula:

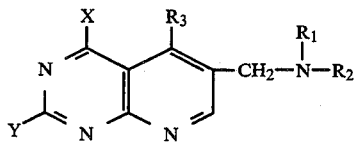

wherein x and y are the same or different and are selected frown the group consisting of OH and NH$_2$; wherein R$_1$ is selected from the group consisting of hydrogen, a first lower alkyl group, a nitroso group and formyl group; wherein R$_2$ is selected from the group consisting of a second lower alkyl group which is the same as or different than said first lower alkyl group, an aryl group, an alkylaryl group, a substituted aryl group and a substituted alkylaryl group, and each substituent of said substituted aryl group or said substituted alkylaryl group is the same as or different and is selected frown the group consisting of a third lower alkyl group which is the same as or different than said first lower alkyl group or said second lower alkyl group, an alicyclichydrocarbon selected from the group consisting of cyclopropyl, cyclobutyl, cyclopentyl and cyclohexyl, an alkoxy group, an alkoxyaryloxy group and a halogen; and wherein R$_3$ is a fourth lower alkyl group which is the same or different than first lower alkyl group, said second lower alkyl group or said third lower alkyl group.

2. A compound and pharmaceutically acceptable salts of claim 1 wherein said first lower alkyl group has one to about seven carbon atoms; wherein said second lower alkyl group has one to about seven carbon atoms; wherein said third lower alkyl group has one to about seven carbon atoms; wherein said fourth lower alkyl group has one to about seven carbon atoms; wherein said alkylaryl group is selected from the group consisting of an alkylphenyl and alkylbenzyl group; wherein said substituted aryl group is selected from the group consisting of a mono-, di- and tri-substituted aryl group; wherein said substituted alkylaryl group is selected from the group consisting of a mono-, di- and tri-substituted alkylphenyl and alkylbenzyl group; and wherein each substituent is the same or different and is selected from the group consisting of methyl, ethyl, n-propyl, n-butyl, methoxy group, chlorine atom, bromine atom and fluorine atom.

3. A compound and pharmaceutically acceptable salts of claim 1 wherein X and Y are each NH$_2$, R$_1$ is H, R$_2$ is 3,4,5-trimethoxyphenyl and R$_3$ is CH$_3$.

4. A compound and pharmaceutically acceptable salts of claim 1 wherein X and Y are each NH$_2$, R$_1$ is CH$_3$, R$_2$ is 3,4,5-trimethoxyphenyl and R$_3$ is CH$_3$.

5. A compound and pharmaceutically acceptable salts of claim 1 wherein X and Y are each NH$_2$, R$_1$ is CHO, R$_2$ is 3,4,5-trimethoxyphenyl and R$_3$ is CH$_3$.

6. A method of therapeutically treating a patient for an illness consisting of employing a compound and a pharmaceutically acceptable salt thereof having the formula:

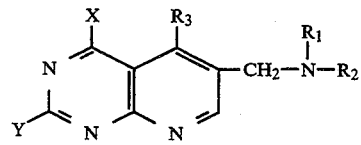

wherein x and y are the same or different and are selected from the group consisting of OH and NH$_2$; wherein R$_1$ is selected from the group consisting of hydrogen, a first lower alkyl group, a nitroso group and a formyl group and wherein R$_2$ is selected from the group consisting of a second lower alkyl group which is the same as or different than said first lower alkyl group, an aryl group, an alkylaryl group, and each substituent of said substituted aryl group or said substituted alkylaryl group is the same as or selected from the group consisting of a third lower alkyl group which is the same as or different than said first lower alkyl group or said second lower alkyl group, an alkoxy group, a substituted alkoxyaryloxy group and a halogen, wherein R$_3$ is a fourth lower alkyl group which is the same as or different than said first lower alkyl group, said second lower alkyl group or said third lower alkyl group;

incorporating said compound in a suitable pharmaceutical carrier, administering a therapeutically effective amount of said compound incorporated in said carrier to a patient; and employing said method in prophylactically treating a patient to provide protection against an illness selected from the group consisting of *Pneumocystis carinii* and *Toxoplasmosis gondii.*

7. The method of claim 6 including employing said carrier selected from the group consisting of physiologic saline and 5% dextrose for injection.

8. The method of claim 6 including administering said compound incorporated in said carrier to a patient by the parenteral route.

9. The method of claim 6 including administering said compound incorporated in said carrier to a patient by the oral route.

10. The method of claim 6 including administering said compound incorporated in said carrier to a patient topically.

11. A method consisting of prophylactically administering to a patient a compound and a pharmaceutically acceptable salt thereof having the formula:

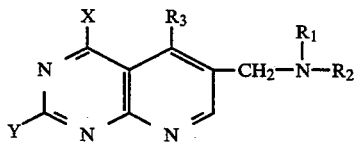

wherein x and y are the same or different and are selected from the group consisting of OH and $HN_2$; wherein $R_1$ is selected from the group consisting of hydrogen, a first lower alkyl group, a nitroso group and a formyl group and wherein $R_2$ is selected from the group consisting of a second lower alkyl group which is the same as or different than said first lower alkyl group, an aryl group, an alkylaryl group, and each substituent of said substituted aryl group or said substituted alkylaryl group is the same or different and is selected from the group consisting of a third lower alkyl group which is the same as or different than said first lower alkyl group or said second lower alkyl group, an alkoxy group, a substituted alkoxyaryloxy group and a halogen, wherein $R_3$ is a fourth lower alkyl group which is the same as or different than said first lower alkyl group, said second lower alkyl group or said third lower alkyl group;
  incorporating said compound in a suitable pharmaceutical carrier,
  administering a prophylactically effective amount of said compound incorporated in said carrier to a patient who is immunocompromised; and
  employing said method in prophylactically treating a patient to provide protection against an illness selected from the group consisting of *Pneumocystis carinii* and *Toxoplasmosis gondii*.

12. The method of claim 11 including employing said carrier selected from the group consisting of physiologic saline and 5% dextrose for injection.

13. The method of claim 11 including administering said compound incorporated in said carrier to a patient by the parenteral route.

14. The method of claim 11 including administering said compound incorporated in said carrier to a patient by the oral route.

15. The method of claim 11 including administering said compound incorporated in said carrier to a patient topically.

* * * * *

UNITED STATES PATENT AND TRADEMARK OFFICE
CERTIFICATE OF CORRECTION

PATENT NO. : 5,346,900
DATED : September 13, 1994
INVENTOR(S) : Aleem Gangjee

It is certified that error appears in the above-indentified patent and that said Letters Patent is hereby corrected as shown below:

Column 10, line 10, "At-H" should be -- Ar-H --.

Column 10, line 12, "$C_{19}H_{24}N_6O_3 \cdot 0.3$" should be -- $C_{19}H_{24}N_6O_3 \cdot 0.3$ --.

Column 10, line 28, "At-H" should be -- Ar-H --.

Column 10, line 31, "$C_{19}H_{23}N_6O_4 \cdot 1.0$" should be -- $C_{19}H_{23}N_6O_4 \cdot 1.0$ --.

Column 11, line 36, "frown" should be -- from --.
Column 11, line 46, "frown" should be -- from --.

Column 12, line 37, "as or" should be —or different and is—

Signed and Sealed this

Fourteenth Day of March, 1995

*Attest:*

BRUCE LEHMAN

*Attesting Officer*     *Commissioner of Patents and Trademarks*